(12) United States Patent
Knott et al.

(10) Patent No.: US 7,015,177 B2
(45) Date of Patent: Mar. 21, 2006

(54) SOLID FORMULATION

(75) Inventors: Richard David Knott, Maidstone (GB); Rowena Roshanthi Landham, Maidstone (GB); Eric Van Der Drift, Enkhuizen (NL)

(73) Assignee: Syngenta Limited, (GB)

( * ) Notice: Subject to any disclaimer, the term of this patent is extended or adjusted under 35 U.S.C. 154(b) by 107 days.

(21) Appl. No.: 10/471,704

(22) PCT Filed: Mar. 13, 2002

(86) PCT No.: PCT/GB02/01146

§ 371 (c)(1),
(2), (4) Date: Feb. 4, 2004

(87) PCT Pub. No.: WO02/074080

PCT Pub. Date: Sep. 26, 2002

(65) Prior Publication Data

US 2004/0137030 A1    Jul. 15, 2004

(30) Foreign Application Priority Data

Mar. 15, 2001 (GB) .................................. 0106469

(51) Int. Cl.
*A01N 25/10* (2006.01)
*A01N 25/14* (2006.01)
*A01N 25/34* (2006.01)

(52) U.S. Cl. ...................... 504/343; 504/360; 504/367; 514/229.2; 514/269; 514/345; 514/521; 514/531; 514/772; 514/772.3; 514/961; 424/501

(58) Field of Classification Search .............. 504/343, 504/360, 367; 514/229.2, 269, 345, 521, 514/531, 772, 772.3, 961; 424/501
See application file for complete search history.

(56) References Cited

U.S. PATENT DOCUMENTS 5,645,847 A      7/1997   Cannelongo ................ 424/408
6,221,368 B1 *   4/2001   Breitenbach et al. ....... 424/400

FOREIGN PATENT DOCUMENTS

GB      2230954      11/1990
WO      9921419      5/1999

* cited by examiner

*Primary Examiner*—S. Mark Clardy
(74) *Attorney, Agent, or Firm*—Thomas Hamilton

(57) ABSTRACT

A solid formulation of an agrochemical is prepared by forming a melt containing at least one agrochemical and at least one thermoplastic binder having a melting point or glass temperature of greater than 35° C., briquetting the melt by dividing it into drops in a first step and solidifying these drops by cooling in a second step, characterized in that the melt additionally comprises a liquid non-volatile solvent for the agrochemical.

29 Claims, No Drawings

SOLID FORMULATION

This application is a 371 of International Application No. PCT/GB02/01146 filed Mar. 13, 2002, which claims priority to GB 0106469.0, filed Mar. 15, 2001, the contents of which are incorporated herein by reference.

This invention relates to a solid formulation and in particular to a solid agrochemical formulation.

In WO 99/21419 there is disclosed a solid formulation of an agrochemical obtainable by preparing a melt comprising from 1 to 80% by weight of an active compound usable in crop protection or a combination of such active compounds; 20 to 99% by weight of at least one thermoplastic binder having a melting point or glass temperature of more than 70° C.; and 0 to 20% by weight of additives, the sum of all the ingredients being 100% by weight and subsequent briquetting by dividing the thermoplastic melt into drops in a first step and solidifying the drops by cooling in a second step. Briquetting of melts of high viscosity with the aid of a Rotoformer (Rotoformer is a trademark of Sandvik Process Systems GMbH, Stuttgart) is known and is described for example in U.S. Pat. No. 4,279,579. Briquettes are solid shaped articles ("buttons") which are formed when a material of high viscosity, while passing through one or more openings or by means of any other division process, is divided into small drop-like amounts which are subsequently cooled to solid shaped articles, for example on a moving transport surface. Buttons formed for example by a Rotoformer are a very useful solid presentation for an agrochemical. The diameter is readily controlled in the range for example of 1 to 35 mm and the buttons so formed are easy to disperse when a suitable thermoplastic binder is used. The buttons are of a consistent size giving more accurate dosing and efficient packing. The buttons are generally heat stable and dust-free and can be formed in a high throughput process.

WO 99/121419 does not include polyethylene glycol in its list of suitable thermoplastic binders, and on page 2, lines 31 to 42 the description refers to WO 93/25074 which is stated to describe formulation by means of a Rotoformer using polyethylene glycol as binder for compounds such as diuron. WO 99/21419 states that such melts are unsatisfactory and did not result in any "solid solution" on solidification.

Solid presentations of low-melting solid agrochemicals frequently suffer from a problem of crystallisation of the agrochemical ingredient. Thus whilst it may be possible to produce an apparently satisfactory solid formulation, it is often the case that crystallisation is initiated over the timescale that solid formulations are typically stored in commercial practice. Once small crystals are nucleated, they may grow rapidly and tend to migrate to the surface of the solid presentation. The consequence is greatly increased operator exposure to the agrochemical and potential release of essentially undiluted solid agrochemical to the environment. The formation of large crystals of agrochemical may also reduce the ability of the solid formulation to dissolve or disperse readily in water to form an acceptable spray solution.

We have found that crystallisation of a water-insoluble, low-melting solid agrochemical may take place within as little as 10 days when a solid presentation is formed using the process such as that described in WO 93/255074 and WO 99/21419.

According to the present invention there is provided a process for preparing a solid formulation of an agrochemical which comprises forming a melt containing at least one agrochemical and at least one thermoplastic binder having a melting point or glass temperature of greater than 35° C., briquetting the melt by dividing it into drops in a first step and solidifying these drops by cooling in a second step, characterised in that the melt additionally comprises a liquid non-volatile solvent for the agrochemical.

The way in which the melt is prepared is not crucial and the solid agrochemical and the solid binder may be mixed together and then melted or separate pre-melts may be mixed or one solid may be added to the melt of the other. In some circumstances it may be preferred to add solid agrochemical to the melt of the binder since the agrochemical may be partially soluble in the binder melt or the binder melt may otherwise depress the melting point of the agrochemical.

We have found that not only does the process of the present invention provide a solid presentation in which no crystallisation of agrochemical is observed over an extended period, but also the solid presentation, for example the buttons, remain non-sticky and without significant agglomeration in storage. This is particularly surprising in view of the fact that high levels of liquid solvent are retained in the button and that the thermoplastic binder may have a melting point or glass transition temperature below that described in WO 99/21419. Furthermore despite the presence of liquid solvent component and the potential use of a thermoplastic binder of lower melting point or glass transition temperature, we have not encountered any problem with solidification of the melt and the process of the present invention provides substantially non-tacky buttons. It is a particular economic advantage of the process of the invention that melt solidification is involved and that heat does not have to be supplied for the evaporation of a solvent such as water.

Whilst it is preferred on economic and environmental grounds that only a minor proportion of the liquid non-volatile solvent for the agrochemical is lost by evaporation during the processing of the melt, a solvent is "non-volatile" as that term is used herein provided that at least a proportion of the solvent remains in final product. The solvent should be liquid under ambient conditions and whilst the scope of the present invention is not to be taken to be limited by any one particular theory, it is believed that the agrochemical remains in solution in the solvent within the confines of the solid presentation, although there may in addition be complex interaction with the solid thermoplastic binder. It is probable that this is the determining factor in preventing crystallisation.

The term "agrochemical" as used herein includes any crop protection or public health active ingredient or any adjuvant used to enhance the bioperformance of a crop protection or public health active ingredient. The term includes a mixture of active ingredients, a mixture of adjuvants or a mixture of one or more active ingredients and one or more adjuvants. Typical agrochemicals include herbicides, plant growth regulants, insecticides (which term includes agents for the control of mites or nematodes), and fungicides. As noted above, the present invention solves or mitigates problems of crystal formation and growth which are particularly prevalent with low-melting agrochemicals and in particular low-melting agrochemicals having a low water solubility. Thus in one embodiment the process of the present invention is particularly suitable for agrochemicals having a a melting point below 120° C. and in particular below 80° C. and in particular for such agrochemicals which have a low water solubility, for example a solubility in water at 25° C. of less than 10 mg/ml, for example less than 1 mg/ml and in particular less than 0.1 mg/ml. Examples of such agrochemicals include insecticides such as tefluthrin (melting point 43° C.), lambda cyhalothrin (melting point 49° C.) and its constituent isomers, pirimicarb (melting point 92° C.), strobilurin fungicides such as azoxystrobin (melting point 116° C.), picoxystrobin (melting point 74° C.) and tralkoxydim (melting point 106° C.). The process of the present invention is particularly applicable to the formation of solid presentations of lambda cyhalothrin, an active ingredient which is especially prone to crystallisation problems in solid presentations. References herein to lambda cyhalothrin include its constituent isomers and in particular (S)-α-cyano-3-phenoxybenzyl (Z)-(1R,3R)-3-(2-chloro-3,3,3-trifluoropropenyl)-2,2-dimethylcyclopropanecarboxylate (gamma cyhalothrin).

The advantages of process of the present invention are not however restricted to the use of low-melting agrochemicals. Agrochemicals having a melting point above 120° C. may nevertheless be soluble in a melt of the thermoplastic binder and solvent at a much lower temperature. We have found for example that thiamethoxam, despite having a melting point of 139° C. is readily soluble in a melt comprising polyethylene gycol and methyl oleate as solvent maintained at about 65 to 70° C. and forms a clear liquid melt at this temperature. Indeed, it is not essential for agrochemical to be soluble in the melt and the agrochemical may be present in part or wholly in the form of a solid dispersion. For all such presentations we have found that the presence of the solvent in combination with the thermoplastic binder provides advantageous button-forming properties. When a thermoplastic binder with low glass transition temperature such as polyethylene glycol is used, non-sticky buttons may be formed at an advantageously low processing temperature.

Further examples of agrochemicals which may be used in the process of the present invention will occur to those skilled in the art and include for example Acequinocyl, Acaricide, m.p. 59.6; Aclonifen, Herbicide, m.p. 81–82; Acrinathrin, Acaricide, Isecticide, m.p. 82.5; AKH-7088, Herbicide, m.p. 57.7–58.1; Alachlor, Herbicide, m.p. 40.5–41.5; Alanycarb, Insecticide, m.p. 46.8–47.2; Ametryn, Herbicide, m.p. 86.3–87.0; Amitraz, Acaricide, Insecticide, m.p. 86–88; Ancymidol, Plant growth regulator, m.p. 110–111; Anilofos, Herbicide, m.p. 50.5–52.5; Azaconazale, Fungicide, m.p. 112.6; Azinphos-ethyl, Insecticide, Arcaricide, m.p. 50; Azinophos-methyl, Insecticide, m.p. 73; Azoxystrobin, Fungicide, m.p. 116; Beflubutamid, Herbicide, m.p. 75; Benalaxyl, Fungicide, m.p. 78–80; Bendiocarb, Insecticide, m.p. 124.6–128.7 Benfluralin, Herbicide, m.p. 65–66.5; Benfurestate, Herbicide, m.p. 30.1; Benoxacor, Herbicide safener, m.p. 107.6; Bensulide, Herbicide, m.p. 34.4; Bensultap, Insetticide, m.p. 83–84; Benzoximate, Acaricide, m.p. 73; Bifenazate, Acaricide, m.p. 120–124; Bifenox, Herbicide, m.p. 84–86; Bifenthrin, Insecticide, Acaricide, m.p. 68–70.6; Bioresmethrin, Insecticide, m.p. 32; Biphenyl, Fungicide, m.p. 69–71; Bromopropylate, Acaricide, m.p. 77; Bromuconazole, Fungicide, m.p. 84; Bupirimate, Fungicide, m.p. 50–51; Buprofezin, Insecticide, Acaricide, m.p. 104.5–105.5; Butafenacil, Herbicide, m.p. 113; Butralin, Herbicide, Plant growth regulator, m.p. 61; Butroxydim, Herbicide, m.p. 80.8; Cafenstrole, Herbicide, m.p. 114–116; Carbetamid, Herbicide, m.p. 119; Carboxin, Fungicide, m.p. 91.5–92.5; CGA 50 439, Acaricide, Ixodicide, m.p. 44; Chlorbromuron, Herbicide, m.p. 95–97; Chlordane, Insecticide, m.p. 104–107; Chlorfenapyr, Insecticide, Acaricide, m.p. 100–101; Chlorpropham, Herbicide, Plant growth regulator, m.p. 41.4; Chlorpyrifos, Insecticide, m.p. 42–43.5; Chlorpyrifos-methyl, Insecticide, Acaricide, m.p. 45.5–46.5; Chlozolinate, Fungicide, m.p. 112.6; Cinidonethyl, Herbicide, m.p. 112.2–112-7; Clodinafop-propargyl, Herbicide, m.p. 59.5; Cloquintocet-mexyl, Herbicide safener, m.p. 69.4; Codlemone, Insect pheromone, m.p. 32; Coumaphos, Insecticide, m.p. 95; Cycloxydim, Herbicide, m.p. 41; Cyfluthrin, Insecticide, m.p. 64–101; Beta-Cyfluthrin, Insecticide, m.p. 81–106; Cyhalofop-butyl, Herbicide, m.p. 50; Cypermethrin, Insecticide, m.p. 61–83; Alpha-Cypermethrin, Insecticide, m.p. 78–81; Beta-Cypermethrin, Insecticide, m.p. 64–71; Theta-Cypermethrin, Insecticide, m.p. 81–87; Cyproconazole, Fungicide, m.p. 106–109; Cyprodinil, Fungicide, m.p. 75.9; 2,4-DB, Herbicide, m.p. 117–119; DDT, Insecticide, m.p. 108.5–109; Deltamethrin, Insecticide, m.p. 100–102; Desmedipham, Herbicide, m.p. 120; Dichlofluanid, Fungicide, m.p. 106; Dichlorprop, Herbicide, m.p. 116–117.5; Dichlorprop-P, Herbicide, m.p. 121–123; Diclofop-methyl, Herbicide, m.p. 39–41; Dicofol, Acaricide, m.p. 78.5–79.5; Diethofencarb, Fungicide, m.p. 100.3; Difenoconazole, Fungicide, m.p. 78.6; Diflumetorim, Fungicide, m.p. 46.8–48.7; Dimepiperate, Herbicide, m.p. 38.8–39.3; Dimethametryn, Herbicide, m.p. 65; Dimethyvinphos, Insecticide, m.p. 69–70; Dinitramine, Herbicide, m.p. 98–99; Dinobuton, Acaricide, Fungicide, m.p. 61–62; Diphenylamine, Fungicide, m.p. 53–54; Dithiopyr, Herbicide, m.p. 65; Dodemorph, Fungicide, m.p. 71; Edifenphos, Fungicide, m.p. -25; EPN, Insecticide, Acaricide, m.p. 34.5; Ergocalciferol, Rodenticide, m.p. 115–118; Esfenvalerate, Insecticide, m.p. 59.0–60.2; Ethalflurallin, Herbicide, m.p. 55–56; Ethofumesate, Herbicide, m.p. 70–72; Ethychlozate, Plant growth regulator, m.p. 76.6–78.1; Etobenzanid, Herbicide, m.p. 92–93; Etofenprox, Insecticide, m.p. 36.4–38.0; Etoxazole, Acaride, m.p. 101–102; Etridiazole, Fungicide, m.p. 19.9; Famphur, Insecticide, m.p. 522.–53.5; Fenamiphos, Nematicide, m.p. 49.2; Fenarimol, Fungicide, m.p. 117–119; Fenazaquin, Acaricide, m.p. 77.5–80; Fenbuconazole, Fungicide, m.p. 124–126; Fenchlorazole-ethyl, Herbicide safener, m.p. 108–112; Fenclorim, Herbicide safener, m.p. 96.9; Fenfuram, Fungicide, m.p. 109–110; Fenobucarb, Insecticide, m.p. 31–32; Fenothiocarb, Acaricide, m.p. 40–41; Fenoxaprop-P-ethyl, Herbicide, m.p. 89–91; Fenoxycarb, Insecticide, m.p. 53–54; Fenpropathrin, Acaricide, Insecticide, m.p. 45–50; Fenpyroximate, Acaricide, m.p. 101.1–102.4; Fentin, Fungicide, Algicide, molluscicide, m.p. 118–120; Fenrtazamide, Herbicide, m.p. 79; Fenvalerate, Insecticide, Acaricide, Ixodicide, m.p. 39.5–53.7; Flamprop-M, Herbicide, m.p. 72.5–86; Fluazinam, Fungicide, m.p. 115–117; Fluazolate, Herbicide, m.p. 79.5–80.5; Fluchloralin, Herbicide, m.p. 42–43; Flufenacet, Herbicide, m.p. 75–77; Flumetralin, Plant growth regulator, m.p. 101.0–103.0; Flumiclorac-pentyl, Herbicide, m.p. 88.9–90.1; Fluoroglycofen-ethylen, Herbicide, m.p. 65; Flurazole, Herbicide safener, m.p. 51–53; Flurenol, Herbicide, m.p. 71; Flurochlordone, Herbicide, m.p. 40.9; Fluroxypyr (-mepthyl), Herbicide, m.p. 58.2–60; Flurprimidol, Plant growth regulator, m.p. 93.5–97; Flusilazole, Fungicide, m.p. 53–55; Fluthiacetmethyl, Herbicide, m.p. 105.0–106.5; Flutolanil, Fungicide, m.p. 104–105; Furalaxyl, Fungicide, m.p. 70–84; Furilzole, Herbicide safener, m.p. 96.6–97.6; Haloxyfop, Herbicide, m.p. 107–108; Gamma HCH, Insecticide, m.p. 112.86; Heptachlor, Insecticide, m.p. 95–96; Hexaconazole, Fungicide, m.p. 110–112; Hexythiazox, Acaracide, m.p. 108.0–108.5; Hydroprene, Insecticide, m.p. Liquid; Imazalil, Fungicide, m.p. 52.7; Imazamethabenz-methyl, Herbicide, m.p. 113–153; Imibencolazole, Fungicide, m.p. 89.5–90; Indanofan, Herbicide, m.p. 60.0–61.1; 4-indol-3-ylbutyric acid, Plant growth regulator, m.p. 123–125; Indoxacarb, Insecticide, m.p. 88.1; Ipconazole, Fungicide, m.p. 88–90; Isoprocarb, Insecticide, m.p. 93–96; Isopropy O-(methoxyamino thiophosphoryl) salicylate, Insecticide, m.p. 45–46; Isoprothiolane, Fungicide, Plant growth regulator, m.p. 54–54.5; Isouron, Herbicide, m.p. 119–120; Kinoprene, Insect growth regulator, m.p. 115–116; Lactofen, Herbicide, m.p. 44–46; Linuron, Herbicide, m.p. 93–95; MCPA, Herbicide, m.p. 119–120.5; MCPA-thioethyl, Herbicide, m.p. 41–42; Mefenpyr-diethyl, Herbicide safener, m.p. 50–52; Mepronil, Fungicide, m.p. 92–93; Metazachlor, Herbicide, m.p. 85; Metconazole, Fungicide, m.p. 110–113; Methabenz thiazuron, Herbicide, m.p. 119–121; Methidathion, Insecticide, Acaricide, m.p. 39–40; Methiocarb, Mollucicide, Insecticide, Acaricide, Bird repellent, m.p. 119; Methoxychlor, Insecticide, m.p. 89; Methyldymron, Herbicide, m.p. 72; Metobenzuron, Herbicide, m.p. 101–102.5; Metobromuron, Herbicide, m.p. 95.5–96; Metominostrobin, Fungicide, m.p. 87–89; Monolinuron, Herbicide, m.p. 80–83; Myclobutanil, Fungicide, m.p. 63–68; Napropamide, Herbicide, m.p. 74.8–75.5; Neburon, Herbicide, m.p. 102–103; Nitrapyrin, Bactericide, nitrification inhibitor, m.p. 62.5–62.9; Nitrothal-isopropyl, Fungicide, m.p. 65; Nonanoic acid, Herbicide, Plant growth regulator, m.p. 12; Oxabetrnil, Herbicide safener, m.p. 77.7; Oxadiazon, Herbicide, m.p. 87; Oxpoconazole fumerate, Fungicide, m.p. 123.6–124.5; Oxyfluorphen, Herbicide, m.p. 85–90; Parathion-methyl, Insecticide, m.p. 35–36; Pendimethalin, Heribcide, m.p. 54–58; Pentanochlor, Herbicide, m.p. 85–86; Pentoxazone, Herbicide, m.p. 104; Permethrin, Insecticide, m.p. 34–35; 2-Phenylphenol, Fungicide, m.p. 57; Phosalone, Insecticide, Acaricide, m.p. 42–48; Phosmet, Insecticide, Acaricide, m.p. 72.0–72.7; Picolinafen, Herbicide, m.p. 107.2–107.6; Pindone, Rodenticide, m.p. 108.5–110.5; Polynactins, Acaricide, m.p. 111–112; Prochloraz, Fungicide, m.p. 46.5–49.3; Prodiamine, Herbicide, m.p. 122.5–124; Prometon, Herbicide, m.p. 91–92; Prometryn, Herbicide, m.p. 118–120; Propachlor, Herbicide, m.p. 77; Propanil, Herbicide, m.p. 91.5; Propaquizafop, Herbicide, m.p. 66.3; Propham, Herbicide, Plant growth regulator, m.p. 87.0–87.6; Pyrazolynate, Herbicide, m.p. 117.5–118.5; Pyrazophos, Fungicide, m.p. 51–52; Pyrazoxyfen, Herbicide, m.p. 111–112; Pyributicarb, Herbicide, Fungicide, m.p. 85.7–86.2; Pyridaben, Insecticide, Acaricide, m.p. 111–112; Pyriaphenthion, Insecticide, Acaricide, m.p. 54.5–56.0; Pyrifenox, Fungicide, m.p. Liquid; Pyrimethanil, Fungicide, m.p. 96.3; Pyrinidifen, Acaricide, Insecticide, m.p. 69.4–70.9; Pyriminobac-methyl, Herbicide, m.p. 105; Quinoxyfen, Fungicide, m.p. 106–107.5; Quizalofop, Herbicide, m.p. 91.7–92.1; Quizalofop-P, Herbicide, m.p. 76.1–77.1; Resmethrin, Insecticide, m.p. 56.5; Silthiofam, Fungicide, m.p. 86.1–88.3; Simetryn, Herbicide, m.p. 82–83; Pinosat, Insecticide, m.p. 84–99.5; Sulfentrazone, Herbicide, m.p. 121–123; Sulfur, Fungicide, Acaricide, m.p. 114.5; Tebuconazole, Fungicide, m.p. 105; Tebufenpyrad, Acaricide, m.p. 61–62; Tecnazene, Fungicide, Plant growth regulator, m.p. 99; Temephos, Insecticide, m.p. 30.0–30.5; Tepraloxydim, Herbicide, m.p. 74; Terbumeton, Herbicide, m.p. 123–124; Terbutryn, Herbicide, m.p. 104–105; Tetrachlorvinphos, Insecticide, Acaricide, m.p. 94–97; Tetramethrin, Insecticide, m.p. 68–70; Thenylchlor, Herbicide, m.p. 72–74; Thiazopyr, Herbicide, m.p. 77.3–79.1; Tolclofos-methyl, Fungicide, m.p. 78–80; Tolylfluanid, Fungicide, m.p. 93; Tralkoxydim, Herbicide, m.p. 106; Triadimefon, Fungicide, m.p. 78–82; Tri-allate, Herbicide, m.p. 29–30; Triazamate, Insecticide, m.p. 54; Trietazine, Herbicide, m.p. 102–103; Trifloxystrobin, Fungicide, m.p. 72.9; Trifluralin, Herbicide, m.p. 48.5–49; Trimethacarb, Insecticide, Molluscicide, m.p. 105–114; Vinclozolin, Fungicide, m.p. 108; Vitamin B 3, Rodenticide, m.p. 84–85; XMC, Insecticide, m.p. 99; Xylylcarb, Insecticide, m.p. 79–80.

One skilled in the art will be able to select a suitable solvent for the agrochemical. It is desirable that the solvent is stable at the melt temperature used and is compatible with the thermoplastic binder such that a homogeneous melt is formed Preferably the solvent dissolves sufficient of the agrochemical to provide the desired loading of agrochemical in the final solid presentation. The selection of the solvent will be illustrated by way of example with particular reference to the agrochemical lambda cyhalothrin, although the solvents listed have broad applicability to a wide range of agrochemicals suitable for use in the process of the present invention Commercially effective solid presentations of lambda cyhalothrin generally contain from about 2.5% active ingredient by weight to about 5% by weight of active ingredient. There is a commercial need for solid presentations containing higher loadings, for example about 10% by weight, but this has hitherto been difficult to achieve. Using the process of the present invention it is possible to obtain a loading of at least 10% and in many instances 20% or higher of lambda cyhalothrin in the final solid product. Use of excessive levels of solvent in the process of the present invention, for example greater than about 40% to 50% w/w in the melt, is likely to lead to a sticky product and this therefore places an upper limit on the amount of solvent that can be used and, depending on the solubility of the agrochemical in the solvent, will determine the maximum concentration of the agrochemical in the melt and in the resultant button. Thus for example if a 10% loading of lambda cyhalothrin is required in the solid product and the solvent content of the melt or final product is 20% w/w, then 10 parts of lambda cyhalothrin must be soluble in 20 parts of solvent, giving a desired solubility of 10 in 30 or 33%. It is not of essential to operate at the limit of the solubility of the agrochemical in the solvent and if desired concentrations of agrochemical above the solubility limit may be used. Surprisingly, the buttons resulting from such melts do not exhibit crystallisation of the active ingredient. In some instances, even though the solubility limit of the agrochemical in the solvent may be exceeded, a homogeneous melt may still be obtained as a result of the combined solvent power of the solvent and the molten thermoplastic binder. As noted above, it is also possible for excess agrochemical to be present in the melt as a dispersed solid.

It is an additional feature of the use of lambda cyhalothrin that undesirable epimerisation of the isomers may take place at high pH and solvents are preferably of pH below about 7. If desired the system may be acidified to a pH of for example below about pH 6 by the addition of a suitable acidifying agent such as citric acid. We have found that citric acid melts or is otherwise soluble in the melt to form a homogeneous melt system.

The solvent should be liquid at ambient temperature and where polymeric solvents are specified, the molecular weight should be such that the solvent is liquid at ambient temperature. Mixtures of solvents may be used. Suitable solvents for use in the process of the present invention include phosphate esters, propylene carbonates, phthalates, methyl esters of fatty acids, polypropylene glycols, polystyrene glycol fatty acid esters, ethoxylated fatty acid methyl esters, N-alkyl pyrrolidones and liquid paraffin. Such solvents are particularly suitable for example when using lambda cyhalothrin as the agrochemical. Examples of suitable phosphate esters include cresyl diphenyl phosphate, tri-n-butyl phosphate, 2-ethylhexyl diphenyl phosphate and tributoxyethyl phosphate. The solubility (% w/w) of lambda cyhalothrin in such solvents is generally of the order of 20% to 40% at 10° C.

Examples of suitable propylene carbonates include 4-methyl-dioxolanone-2-one. Examples of suitable phthalates include benzyl butyl phthalate. Examples of suitable methyl esters of fatty acids include methyl oleate, methyl laurate and methyl soyate. Examples of suitable polyethylene glycol fatty acid esters include PEG-300 monopelargonate, PEG 200 mono-oleate, PEG-300 mono-oleate and PEG-400 mono-oleate. Examples of N-alkylpyrolidones include N-methylpyrrolidone, N-octylpyrrolidone and N-dodecylpyrrolidone.

Solvents may be water-miscible, water-immiscible or dispersable in water. Whilst we have obtained very satisfactory results using water-miscible solvents such as N-alkylpyrrolidones, it is believed that water-immiscible solvents, in particular those which disperse readily in water, may generate agrochemical-containing emulsions when the button is dispersed in water ready for spraying. Particularly suitable solvents in this regard are polyethylene glycol fatty acid esters which are readily dispersed in water and form self-emulsifying systems. We have found that buttons formed using a polyethylene glycol fatty acid ester as solvent form very fine emulsion droplets (less than one micron average diameter) with a narrow size distribution when the button is dissolved in water. The button is in consequence readily dispersed in water and the emulsion formed is of excellent stability whilst the agrochemical is effectively and evenly dispersed as a solution in the solvent droplets. Suitable polyethylene glycol fatty acid esters have a fatty acid alkyl chain length of from 6 to 25, for example from 8 to 20 and a polyethylene glycol molecular weight of from 100 to 500, for example from 200 to 400.

In WO 99/21419 it is stated that suitable thermoplastic binders are polymeric binders or binders of low molecular weight which can be processed thermoplastically without decomposition and which, in combination with the active compound and other additives do not give solid forms which are prone to cold flow. Such thermoplastic binders are stated to have a melting point or glass temperature of more than 70° C. and preferably from 80° C. to about 200° C. Such binders are also effective in the process of the present invention and accordingly examples of suitable binders are polyvinylpyrrolidone (PVP); copolymers of N-vinylpyrrolidone (NVP) and vinyl esters, especially vinyl acetate; copolymers of vinyl acetate and crotonic acid; partially hydrolysed polyvinyl acetate; polyvinyl alcohol, poly (hydroxyalkyl acrylates) (for example $C_1$- or $C_2$-alkyl); poly (hydroxyalkyl methacrylates) (for example $C_1$- or $C_2$ alkyl); polyacrylates and polymethacrylates; copolymers of methyl methacrylate and acrylic acid; cellulose ethers, especially methylcellulose and ethylcellulose; hydroxyalkylcelluloses, especially hydroxypropylcellulose; cellulose phthalates, especially cellulose acetate phthalate and hydroxypropylmethylcellusose phthalate; and mannans, especially galactomannans. Mixtures of thermoplastic binders may also be used.

WO 99/21419 does not include polyethylene glycol in its list of suitable thermoplastic binders, and on page 2, lines 31 to 42 the description refers to WO 93/25074 which is stated to describe formulation by means of a Rotoformer using polyethylene glycol as binder for compounds such as diuron. WO 99/21419 states that such melts are unsatisfactory and did not result in any "solid solution" on solidification. Furthermore polyethylene glycol, depending on the molecular weight, may have a melting point or glass temperature of less than the 70° C. specified in WO 99/21419. We have found that, surprisingly in view of the disclosure of WO 99/21419, polyethylene glycol and indeed even polyethylene glycol having a melting point or glass temperature below 70° C. is an excellent thermoplastic binder for use in the process of the present invention and exhibits none of the disadvantages suggested by WO 99/21419 or which might be expected to result from the low melting point or glass transition temperature. Indeed, when used with a low-melting agrochemical such as lambda cyhalothrin, the use of a polyethylene glycol having a melting point or glass temperature of from about 50° C. to about 80° C. permits the formation of a relatively low-temperature melt with consequent cost savings in commercial production. Such relatively low melt temperatures are also highly desirable when the agrochemical has a tendency to degrade at higher temperatures. Thus lambda cyhalothrin has a tendency to degrade at temperatures in excess of 100° C. and melt temperatures in the range from about 50° C. to about 90° C. are therefore highly suitable. Despite the low melt temperature, we have found that buttons thus formed release readily from the substrate onto which they are deposited and remain non-tacky on heating at 50° C. It will be appreciated however that the thermoplastic binder must be solid at ambient temperatures and must therefore have a melting point or glass transition temperature of greater than 35° C. It is desirable that the thermoplastic binder has a melting point or glass transition temperature of greater than 40° C. and preferably greater than 50° C.

Overall therefore the thermoplastic binder for use in the present invention may have a melting point or glass transition temperature of from 40° C. to 200° C. and preferably from 50° C. to 200° C., whilst the particular benefits of the present invention are most apparent when the thermoplastic binder has a melting point or glass transition temperature of from 50° C. to 80° C.

Especially suitable thermoplastic binders therefore include polyethylene glycol having an average molecular weight in the range from about 3400 to about 10,000 (corresponding to a melting point or glass temperature of from 55° C. to 65° C. with a molecular weight of about 8,000 (melting point or glass temperature of 62° C.) being especially preferred. Polyethylene glycol is especially compatible with polyethylene glycol fatty acid esters used as solvent for the agrochemical.

Further thermoplastic binders which may be used in the process of the present invention include polyethoxylated fatty acids and alcohols, ethylene oxide/propylene oxide block copolymers polyethoxylated alkylphenols and long chain fatty acids such as stearic acid (melting point or glass transition temperature 67° C.).

In the process of the present invention the melt is formed into briquettes or "buttons" by dividing it into drops in a first step and solidifying these drops by cooling in a second step. The briquetting suitably takes place by passing the viscous melt through one or more openings, but any process for dividing the melt into droplets may be used. Suitable processes for achieving this briquetting process are known in the art and examples are described for WO 99/21419 and references included therein. Suitable equipment is commercially available. A convenient and commercially available apparatus for carrying out the briquetting process according to the present invention is the Rotoformer supplied by Sandvik Process Systems GmbH. Other processes for dividing the melt into drops in the first step will occur to those skilled in the art and include for example spinning disc techniques.

In a typical small-scale process for use in the present invention, an agrochemical such as lambda cyhalothrin (11.2% w/w) is pre-melted if appropriate and added to a blend comprising EMEREST 2634 (20.0% w/w—PEG-300 monopelargonate) as solvent and TERGITOL XD (1.0% w/w) as surfactant. The blend is well mixed and maintained at a temperature between 65° C. and 70° C. Finally the polyethylene glycol (65.7% w/w, molecular weight 8000) as thermoplastic binder, citric acid (2.0% w/w) if required as an acidifying agent, and if desired a dye (0.1% w/w, waxoline blue) are added to form the melt formulation. Approximately 20 liters of the melt material are added to a holding vessel maintained at 75° C. The melt is processed to form buttons on a Rotoformer manufactured by Sandvik Process Systems under the following conditions: Belt speed: 19 m/min, Screen pitch: 5 mm, Hole size: 1.2 mm, Inlet temp: 59° C. This generates buttons having the following characteristics: Diameter: 3.6 mm, Weight: 9 mg. The melt temperature used will depend on the nature of the agrochemical and the thermoplastic binder. It will be appreciated that the melting point or glass temperature of the thermoplastic binder may be reduced by the presence of the agrochemical, solvent and other additives if present. Selection of the melt temperature for a given system is however a matter of routine optimisation. Melt temperatures will typically range from 55° C. to 120° C. and more particularly from about 65° C. to 80° C. when using polyethylene-glycol as the thermoplastic binder. As noted above clear, even high-melting agrochemicals may be processed at these temperatures either in the form of a homogeneous solution in the melt or as an inhomogeneous dispersion.

Conventional additives may be included in the formulation of the present invention provided that they are compatible with the other components of the melt. In particular it may be desirable to include a surface active agent or dispersant to assist dissolution or dispersal of the solid button in water and to stabilise the aqueous emulsion or dispersion thus formed. Adjuvants may also be added whose primary purpose is to improve the bioefficacy of the agrochemical. Many suitable wetters, dispersants and adjuvants are known in the art. Preferred surface active agents include TERGITOL XD (ethylene oxide/propylene oxide block copolymer), LUBROL 17A17 (fatty alcohol ethoxylate), MORWET D425 (sulphonated alkylnaphthalene formaldehyde condensate, sodium salt), EMPICOL LZ (sodium lauryl sulphate).

Other typical additives include water-soluble or dispersible fillers, colours and stabilizers such as anti-oxidants and light stabilisers. There may be advantages in using additives which are themselves molten at the melt temperature or are otherwise soluble in the melt, thereby forming a homogeneous melt system. This is not however an essential feature of the invention and additives such as dispersible fillers may be used which are dispersed as a finely divided solid in the melt, and hence in the resultant solid product. Such fillers will usually be dispersible rather than soluble in water once the resultant solid product is added to water.

For certain applications a controlled crystallisation of a low-melting agrochemical may actually be desirable. Thus for example if an insecticide such as lambda cyhalothrin is to be used for protectant application to surfaces such as walls and furnishings, the presence of small crystals of lambda cyhalothrin in combination with a filler assists the product to adhere to solid surfaces and limits absorption into a porous surface. In this way, long-term surface activity over a period of months may be maintained. We believe that the use of a filler promotes limited but effective crystallisation whilst the overall process of the invention prevents excessive crystallisation which would limit the dispersability of the button into water.

If desired dispersability of the button in water may be increased by including a gas-generator and an acidic medium. Typical gas-generators include an alkali metal bicarbonate in the presence an acidic medium such as citric acid. Such systems are stable in the melt but generate carbon dioxide in the presence of water, thereby aiding the dispersability of the button.

For the majority of applications the buttons will be dissolved in water in a spray tank and applied using conventional spray equipment The present invention is not so limited however and includes controlled-release buttons which are applied or broadcast directly to the soil or for example to a paddy field. In general the thermoplastic binder used for such applications will have a much lower water-solubility, typically associated with a higher molecular weight. In such applications the agrochemical diffuses slowly out of the encapsulating thermoplastic binder under the action of water in the environment.

Applications for slow-dispersing buttons include for example soil-applied insecticides and the broadcasting of buttons containing an attractant for pest in combination with an agrochemical effective against that pest.

The present invention may be used to form buttons containing seed and an agrochemical protectant for that seed such as thiamethoxam. For such a process the melt temperature should be sufficiently low that the viability of the seed is not compromised. It is for example possible to use polyethylene glycol as the thermoplastic binder for such applications. We have found that the presence of the solvent provides further and expected advantages in such systems. Thus in the presence of the solvent, well-formed and regularly-shaped buttons are produced whilst in the absence of solvent there is a tendency for the button to "curl up" from the substrate on which it is deposited. The solvent may also assist in the release of the button from the plate onto which it is deposited. We have also found that in the presence of solvent the seed tends to be incorporated at the edge of the button thereby allowing access to moisture for germination. We have found that a long-chain fatty acid such as stearic acid is a particularly suitable thermoplastic binder for use with seeds and shows no significant retardation of germination. Liquid paraffin is an example of a suitable solvent for use with stearic acid. If desired the seed may be coated with a filler to improve adhesion between the seed and the thermoplastic binder material forming the button.

The invention is illustrated by the following examples in which all parts and percentages are by weight unless otherwise stated.

EXAMPLE 1

Pre-melted polyethylene glycol (30.4 g, molecular weight 8000—the thermoplastic binder) was added to a blend comprising pre-melted lambda cyhalothrin (5.6 g), N-octyl pyrrolidone (10.0 g—the solvent), TERGITOL XD (0.5 g, ethylene oxide, propylene oxide block copolymer—a non ionic surfactant ), LUBROL 17A17 (2.5 g, fatty alcohol ethoxylate—adjuvant and citric acid (1.0 g—acidifying agent). The final blend was well mixed and maintained at a temperature between 65° C. and 70° C. A dropping pipette was used to deposit drops of the melt onto a stainless steel plate. The drops, typically 5–6 mm in diameter, were allowed to cool to room temperature to form buttons, detached from the metal plate and stored in a PET container.

The dispersion time of the buttons in water was measured by a standard test as follows:

Standard Dispersion Time Test

The dispersion time of the solid was measured by dropping 3 buttons into a boiling tube (of approximate dimensions 8 inches×1 inch, with a water-tight stopper) filled with tap water at 20° C.±1° C. to leave an ullage space of 0.5 to 0.75 inches in the tube. The tube was inverted slowly such that the buttons are not allowed to sit on the bottom of the tube but are allowed to settle through the medium under the influence of gravity. The time taken for the buttons to completely disperse was noted.

As measured by the standard test method given above the dispersion time of a button sample (of dimension 5–6 mm diameter, 1–2 mm dome height) was approximately 6 minutes.

The mean droplet size (D 4,3) of the resultant oil-in-water emulsion was 2.7 microns with 91% of the droplets being less than 5 microns, when measured using a Malvern Mastersizer S.

No caking or tackiness was observed when 10 g of these buttons were stored in a PET container for 17 hours in an oven maintained at 45° C. and then allowed to cool to room temperature.

The buttons were dispersed in water and the resultant emulsion showed excellent bioefficacy when tested against standard insect species.

The dispersion time of these buttons in water and the mean droplet size of the resultant oil-in-water emulsion did not change following storage at room temperature for 5 months. Examination of the aged buttons under the optical microscope showed no evidence of crystallisation of the active ingredient. Storage was continued for a further 5 months after which there was still no sign of crystallisation.

COMPARISON 1

The formulation procedure described in Example 1 was repeated with the exception that the solvent (N octyl pyrrolidone) was omitted and replaced with a higher (equivalent) loading of PEG 8000.

The resultant buttons had very similar initial characteristics to those described in Example 1. However, after only 10 days of storage at room temperature the buttons showed evidence of active ingredient crystallisation accompanied by a significant decrease in water dispersibility.

EXAMPLE 2

Pre-melted polyethylene glycol (32.9 g, molecular weight 8000) was added to a blend comprising pre-melted lambda cyhalothrin (5.6 g), EMEREST 2634 (10.0 g, PEG-300 monopelargonate) as solvent, TERGITOL XD (0.5 g a non-ionic surfactant) and citric acid (1.0 g). The final blend was well mixed and maintained at a temperature between 65° C. and 70° C. A dropping pipette was used to deposit drops of the melt onto a stainless steel plate. The drops, typically 5–6 mm in diameter, were allowed to cool to room temperature, detached from the metal plate and stored in a PET container.

The dispersion time in water, as measured by the standard test, for a 5–6 mm button sample was approximately 5.5 minutes.

The mean droplet size (D 4,3) of the resultant oil-in-water emulsion was 0.86 microns with 100% of the droplets being less than 5 microns, when measured using a Malvern Mastersizer S.

No caking or tackiness was observed when 10 g of these buttons were stored in a PET container for 17 hours in an oven maintained at 45° C. and allowed to cool to room temperature.

The buttons were dispersed in water and the resultant emulsion showed excellent bioefficacy when tested against standard insect species.

The dispersion time of these buttons in water and the mean droplet size of the resultant oil-in-water emulsion did not change following storage at room temperature for 5 months. Examination of the aged buttons under the optical microscope showed no evidence of crystallisation of the active ingredient. Examination of the buttons using an Infra Red microscope revealed that the active ingredient was fully contained within the button and that the external surface of the button was free of active ingredient.

EXAMPLE 3

Pre-melted polymer SYNPERONIC PE F127 (6.7 g, ethoxylated polypropylene oxide ethylene oxide/proplylene oxide block copolymer, molecular weight 12000) was added to a blend comprising pre-melted lambda cyhalothrin (1.1 g), N-methyl pyrrolidone (2.0 g) and citric acid (0.2 g). The final blend was well mixed and maintained at a temperature between 65° C. and 70° C. A dropping pipette was used to deposit drops of the melt onto a stainless steel plate. The drops, typically 5–6 mm in diameter, were allowed to cool to room temperature, detached from the metal plate and stored in a PET container. The buttons dispersed readily in water. No crystallisation was observed after 10 months storage.

EXAMPLE 4

Pre-melted polyethylene glycol (2.0 g, molecular weight 6000) and SYNPERONIC PE F127 (4.0 g), together forming a mixed thermoplastic binder system, were added to a blend comprising azoxystrobin (2.5 g), N-methyl pyrrolidone (0.5 g) and TERGITOL XD (1.0 g). The final blend was well mixed and maintained at a temperature between 65° C. and 70° C. A dropping pipette was used to deposit drops of the melt onto a stainless steel plate. The drops, typically 5–6 mm in diameter, were allowed to cool to room temperature, detached from the metal plate and stored in a PET container.

The buttons dispersed relatively slowly in water.

EXAMPLE 5

This Example illustrates the use of a mixture of two agrochemicals. Pre-melted polyethylene glycol (6.3 g, molecular weight 8000) was added to a blend comprising pre-melted lambda cyhalothrin (0.6 g), EMEREST 2634 (1.0 g), TERGITOL XD (0.1 g) and citric acid (0.2 g). The blend was well mixed and maintained at a temperature between 65° C. and 70° C. Pirimicarb (1.8 g) was mixed in and a clear melt was obtained. A dropping pipette was used to deposit drops of the melt onto a stainless steel plate. The drops, typically 5–6 mm in diameter, were allowed to cool to room temperature, detached from the metal plate and stored in a PET container. The buttons dispersed in water with no residue.

EXAMPLE 6

Pre-melted polyethylene glycol (3.4 g, molecular weight 8000) was added to a blend comprising pre-melted tefluthrin (0.55 g), EMEREST 2634 (1.0 g, PEG-300 monopelargonate) and TERGITOL XD (0.05 g, ethylene oxide, propylene oxide block copolymer). The final blend was well mixed and maintained at a temperature between 65° C. and 70° C. A dropping pipette was used to deposit drops of the melt onto a stainless steel plate. The drops, typically 5–6 mm in diameter, were allowed to cool to room temperature to form buttons which were detached from the metal plate and stored in a PET container.

The buttons were water dispersible. The mean droplet size (D 4,3) of the resultant oil-in-water emulsion was 2.75 microns with 87% of the droplets being less than 5 microns, when measured using a Malvern Mastersizer S. The excellent droplet size distribution indicates that no crystallisation of the tefluthrin had taken place.

EXAMPLE 7

This Example illustrates the use of a reduced amount of solvent such that lambda cyhalothrin forms a supersaturated solution (compare Example 2). Pre-melted polyethylene glycol (35.4 g, molecular weight 8000) was added to a blend comprising pre-melted lambda cyhalothrin (5.6 g), EMEREST 2634 (7.5 g, PEG-300 monopelargonate), TERGITOL XD (0.5 g) and citric acid (1.0 g). The final blend was well mixed and maintained at a temperature between 65° C. and 70° C. A dropping pipette was used to deposit drops of the melt onto a stainless steel plate. The drops, typically 5–6 mm in diameter, were allowed to cool to room temperature to form button which were detached from the metal plate and stored in a PET container at RT for 11 months. After storage, the buttons dispersed readily in water. The mean droplet size (D 4,3) of the resultant oil-in-water emulsion was 0.8 microns with 98% of the droplets being less than 5 microns, when measured using a Malvern Mastersizer S. Despite the use of a reduced amount of solvent the excellent droplet size distribution indicates that no crystallisation had taken place.

EXAMPLE 8

This Example illustrates the use of a high loading of agrochemical (20% by weight of lambda cyhalothrin in the final button as compared with 10% by weight in Examples 2 and 7). Pre-melted polyethylene glycol (57.0 g, molecular weight 8000) was added to a blend comprising pre-melted lambda cyhalothrin (20 g), EMEREST 2634 (20.0 g, PEG-300 monopelargonate), TERGITOL XD (1.0 g) and citric acid (2.0 g). The final blend was well mixed and maintained at a temperature between 65° C. and 70° C. A dropping pipette was used to deposit drops of the melt onto a stainless steel plate. The drops, typically 5–6 mm in diameter, were allowed to cool to room temperature to form buttons which were detached from the metal plate and stored in a PET container for 10 months.

Following storage, the buttons dispersed readily in water and the mean droplet size (D 4,3) of the resultant oil-in-water emulsion was 1.2 microns with 100% of the droplets being less than 5 microns, when measured using a Malvern Mastersizer S.

EXAMPLE 9

This Example illustrates the use of a filler in the composition. Pre-melted polyethylene glycol (65.8 g, molecular weight 8000) was added to a blend comprising pre-melted lambda cyhalothrin (11.2 g), N-methyl pyrrolidone (5.0 g), TERGITOL XD (1.0 g) and citric acid (2.0 g). The blend was well mixed and maintained at a temperature between 65° C. and 70° C. Silica powder (7.5 g, Degussa FK320) and China clay (7.5 g) were then stirred into the melt and mixed thoroughly to give a homogeneous dispersion. A dropping pipette was used to deposit drops of the melt onto a stainless steel plate. The drops, typically 5–6 mm in diameter, were allowed to cool to room temperature to form buttons which were detached from the metal plate and stored in a PET container.

The buttons dispersed readily in water to produce a dispersion that was used to spray both unglazed ceramic tiles and adult German cockroaches.

EXAMPLE 10

Methyl oleate (20.0 g) was added to pre-melted polyethylene glycol (68.0 g, molecular weight 8000). Thiamethoxam (12.0 g) was added to the melt, mixed in and the temperature of the melt maintained between 65° C. and 70° C. until a clear liquid was formed. A dropping pipette was used to deposit drops of this melt onto seeds (cabbage, lettuce and tomato), placed in a row, on a stainless steel plate. On cooling to room temperature, the resulting button contained the seed asymmetrically, such that the seed was embedded on one side of the hemisphere. The coated seed was detached from the metal plate and stored in a PET container.

What is claimed is:

1. A process for preparing a solid formulation of an agrochemical which comprises forming a melt containing at least one agrochemical and at least one thermoplastic binder having a melting point or glass temperature of greater than 35° C., briquetting the melt by dividing it into drops in a first step and solidifying these drops by cooling in a second step, characterised in that the melt additionally comprises a liquid non-volatile solvent for the agrochemical wherein the solvent is a phosphate ester, a propylene carbonate, a phthalate, a methyl ester of a fatty acid, a polystyrene glycol fatty acid ester, an ethoxylated fatty acid methyl ester, polyethylene glycol fatty acid ester, an N-alkyl pyrrolidone or liquid paraffin.

2. A process according to claim 1 wherein the at least one thermoplastic binder is polyvinylpyrrolidone, a copolymer of N-vinylpyrrolidone and a vinyl ester, a copolymer of vinyl acetate and crotonic acid, partially hydrolysed polyvinyl acetate, polyvinyl alcohol, poly (hydroxyalkyl acrylate), poly(hydroxyalkyl methacrylate), polyacrylate, polymethacrylate, copolymers of methyl methacrylate and acrylic acid, cellulose ether, hydroxyalkylcellulose, cellulose phthalate, a mannan, a polyethylene glycol, a polyethoxylated fatty acid, and a polyethoxylated fatty alcohol, an ethylene oxide/propylene oxide block copolymer, a polyethoxylated alkylphenol or a long chain fatty acid.

3. A process according to claim 1 wherein the solvent is a polyethylene glycol fatty acid ester having a fatty acid alkyl chain length of from 6 to 25 and a polyethylene glycol molecular weight of from 100 to 500.

4. A process according to claim 3 wherein the at least one thermoplastic binder is polyethylene glycol.

5. A process according to claim 1 wherein the solid formulation contains seed and the agrochemical is a protectant for that seed.

6. A process according to claim 5 wherein the at least one thermoplastic binder is a long-chain fatty acid and the solvent is liquid paraffin.

7. A process according to claim 1 wherein the at least one thermoplastic binder has a melting point or glass transition temperature of greater than 50° C.

8. A process according to claim 1 wherein the at least one thermoplastic binder has a melting point or glass transition temperature of from 40° C. to 200° C.

9. A process according to claim 8 wherein the at least one thermoplastic binder has a melting point or glass transition temperature of from 50° C. to 80° C.

10. A process according to claim 1 wherein the melt temperature is from 55° C. to 120° C.

11. A process according to claim 10 wherein the at least one agrochemical is thiamethoxam.

12. A process according to claim 11 wherein the at least one agrochemical is thiamethoxam.

13. A process according to claim 1 wherein the at least one agrochemical has a melting point below 120° C.

14. A process according to claim 13 wherein the at least one agrochemical has a low water-solubility.

15. A process according to claim 14 wherein the at least one agrochemical is tefluthrin, lambda cyhalothrin, pirimicarb, axozystrobin, picoxystrobin or tralkoxydim.

16. A process for preparing a solid formulation of an agrochemical which comprises forming a melt containing at least one agrochemical and at least one thermoplastic binder having a melting point or glass temperature of greater than 35° C., briquetting the melt by dividing it into drops in a first step and solidifying these drops by cooling in a second step, characterised in that the melt additionally comprises a liquid non-volatile solvent for the at least one agrochemical wherein the at least one thermoplastic binder is polyethylene glycol and the solvent is a phosphate ester, a propylene carbonate, a phthalate, a methyl ester of a fatty acid, a polystyrene glycol, a polystyrene glycol fatty acid ester, an ethoxylated fatty acid methyl ester, polyethylene glycol fatty acid ester, an N-alkyl pyrrolidone or liquid paraffin.

17. A process according to claim 16 wherein the at least one thermoplastic binder has a melting point or glass transition temperature of greater than 50° C.

18. A process according to claim 2 wherein the at least one thermoplastic binder is polyethylene glycol having an average molecular weight in the range from about 3400 to about 10,000.

19. A process according to claim 16 wherein the at least one thermoplastic binder has a melting point or glass transition temperature of from 40° C. to 200° C.

20. A process according to claim 19 wherein the at least one thermoplastic binder has a melting point or glass transition temperature of from 50° C. to 80° C.

21. A process according to claim 16 wherein the melt temperature is from 55° C. to 120° C.

22. A process according to claim 21 wherein the at least one agrochemical has a melting point above 120° C. and is soluble or dispersible in the melt.

23. A process according to claim 16 wherein the at least one agrochemical has a melting point below 120° C.

24. A process according to claim 23 wherein the at least one agrochemical has a low water-solubility.

25. A process according to claim 24 wherein the at least one agrochemical is tefluthrin, lambda cyhalothrin, pirimicarb, axozystrobin, picoxystrobin or tralkoxydim.

26. A process according to claim 25 wherein the at least one agrochemical is thiamethoxam.

27. A process according to claim 16 wherein the at least one thermoplastic binder is a polyethylene glycol having an average molecular weight in the range from about 3400 to about 10,000.

28. A process according to claim 16 wherein the solvent is a polyethylene glycol fatty acid ester having a fatty acid alkyl chain length of from 6 to 25 and a polyethylene glycol molecular weight of from 100 to 500.

29. A process according to claim 16 wherein the solid formulation contains seed and at least one agrochemical is a protectant for that seed.

* * * * *